United States Patent
Loverich et al.

(10) Patent No.: US 8,928,161 B2
(45) Date of Patent: Jan. 6, 2015

(54) APPARATUSES AND METHODS FOR HARVESTING ENERGY FROM PROSTHETIC LIMBS

(75) Inventors: Jacob J. Loverich, State College, PA (US); David R. Kraige, State College, PA (US); Jeremy E. Frank, Pine Grove Mills, PA (US); Richard T. Geiger, Boalsburg, PA (US)

(73) Assignee: KCF Technologies, Inc., State College, PA (US)

( * ) Notice: Subject to any disclaimer, the term of this patent is extended or adjusted under 35 U.S.C. 154(b) by 228 days.

(21) Appl. No.: 13/481,769

(22) Filed: May 25, 2012

(65) Prior Publication Data
US 2013/0317627 A1    Nov. 28, 2013

(51) Int. Cl.
| | |
|---|---|
| F02B 63/04 | (2006.01) |
| F03G 7/08 | (2006.01) |
| H02K 7/18 | (2006.01) |
| A61F 2/68 | (2006.01) |
| F03G 5/06 | (2006.01) |
| A61F 2/50 | (2006.01) |
| A61F 2/70 | (2006.01) |
| A61F 2/74 | (2006.01) |

(52) U.S. Cl.
CPC ... *A61F 2/68* (2013.01); *F03G 5/06* (2013.01); *H02K 7/1853* (2013.01); *A61F 2002/5006* (2013.01); *A61F 2002/708* (2013.01); *A61F 2002/745* (2013.01)
USPC ...................................................... 290/1 R

(58) Field of Classification Search
CPC ....... F03G 5/06; A61F 2/68; A61F 2002/708; A61F 2002/745; A61F 2002/5006; A61F 2/60; H02K 7/1853; H02K 7/18
USPC ................... 290/1 R, 1 A, 50; 623/26, 24, 27
See application file for complete search history.

(56) References Cited

U.S. PATENT DOCUMENTS

| | | |
|---|---|---|
| 4,065,815 A | 1/1978 | Sen-Jung |
| 4,595,179 A | 6/1986 | Glabiszewski |
| 5,948,021 A | 9/1999 | Radcliffe |
| 6,295,914 B1 | 10/2001 | Iversen |
| 6,517,585 B1 | 2/2003 | Zahedi et al. |
| 6,610,101 B2 | 8/2003 | Herr et al. |

(Continued)

FOREIGN PATENT DOCUMENTS

DE    10 2008 045 113 A1    3/2010

OTHER PUBLICATIONS

Machine translation of DE 10 2008 045 113. May 15, 2014.*

(Continued)

*Primary Examiner* — Javaid Nasri
(74) *Attorney, Agent, or Firm* — Oliff PLC (57) ABSTRACT

An apparatus for harvesting energy from motion of a prosthetic limb, wherein the prosthetic limb has motion in at least one degree of freedom, may include a hydraulic amplifier mechanically coupled with a generator. The hydraulic amplifier may include an input member configured to receive an input motion when a first motion in a degree of freedom of the prosthetic limb causes pressure and motion of hydraulic fluid. The hydraulic amplifier is configured to amplify the input motion of the input member to a greater output motion. The generator is configured to convert mechanical energy of the output motion into corresponding electrical energy delivered to one of an electrical load and an electrical storage reservoir.

20 Claims, 6 Drawing Sheets

(56) References Cited

U.S. PATENT DOCUMENTS

| | | |
|---|---|---|
| 6,740,125 B2 | 5/2004 | Mosler |
| 7,066,964 B2 | 6/2006 | Wild |
| RE39,961 E | 12/2007 | Petrofsky et al. |
| 7,485,152 B2 | 2/2009 | Haynes et al. |
| 7,544,214 B2 | 6/2009 | Gramnas |
| 7,578,799 B2 | 8/2009 | Thorsteinsson et al. |
| 7,618,463 B2 | 11/2009 | Oddsson et al. |
| 7,652,386 B2 | 1/2010 | Donelan et al. |
| 7,659,636 B2 | 2/2010 | Donelan et al. |
| 7,883,548 B2 | 2/2011 | Lang |
| 7,985,265 B2 | 7/2011 | Moser et al. |
| 8,311,632 B2 * | 11/2012 | Pless et al. ............... 607/35 |
| 8,698,329 B2 * | 4/2014 | Loverich et al. ............ 290/1 R |
| 2007/0050044 A1 * | 3/2007 | Haynes et al. ............. 623/24 |
| 2009/0192619 A1 | 7/2009 | Martin et al. |
| 2010/0023133 A1 | 1/2010 | Fairbanks et al. |

OTHER PUBLICATIONS

International Search Report dated Sep. 5, 2013, issued in counterpart International Application No. PCT/US2013/042879.

US Office Action dated Aug. 23, 2013, issued in cross-referenced U.S. Appl. No. 13/481,770.

* cited by examiner

APPARATUSES AND METHODS FOR HARVESTING ENERGY FROM PROSTHETIC LIMBS

GOVERNMENT LICENSE RIGHTS

This invention was made with government support under Contract No. W81XWH-10-C-0192 awarded by the U.S. Army TATRC (U.S. Army Medical Research Acquisition Activity, 820 Chandler St., Fort Detrick, MD 21702-5014). The government has certain right in the invention.

CROSS-REFERENCE TO RELATED APPLICATIONS

The present disclosure is related to copending U.S. patent application Ser. No. 13/481,770, now U.S. Pat. No. 8,698,329, the disclosure of which is incorporated herein by reference.

TECHNICAL FIELD

The present disclosure relates generally to apparatuses and methods for harvesting energy from prosthetic limbs and, more particularly, to hydraulic energy harvesting devices for prosthetic limbs.

BACKGROUND

The field of prosthetic devices has advanced greatly through the years. Many current lower-limb prosthetics use sensors, microprocessor controllers, and valves or other actuators to assist the user's gait motion. The devices range from prosthetics which actively propel the user forward to devices which assist in controlling the motion of the joint. Even if the device does not provide powered motion such as actively propelling the user forward, they may still use energy when in motion to run the valves or other actuators that control the motion of the joint(s). Many of these devices require a power source to operate. The required energy is provided by an onboard battery with a fixed capacity. This battery is limiting to the user because it must be recharged periodically. Many users need to recharge a prosthetic limb daily, although a very active user could conceivably completely discharge the limb in less than a day. Energy harvesting, which is in its infancy in prosthetics, would alleviate the user of this inconvenience.

One issue encountered when designing energy harvesting devices for prosthetics is that only a small amount of deflection is tolerable in a prosthetic limb, therefore limiting the amount of mechanical movement available to move an electromechanical generator as a means of gathering energy. The generator could be directly coupled to the deflecting components, for instance through a series of gears, but the amount of force on some of the components in such a device is often too large for the small electromechanical generator components that can be used in prosthetics, and these high forces can be a significant noise source.

What is currently lacking in the art is an energy harvesting device capable of amplifying the small amount of deflection available when a prosthetic limb is in use to generate a larger mechanical motion that can be used to drive an electromechanical generator while reducing the force exerted on the electromechanical generator. By adding this energy harvesting capability it is possible to partially or fully recharge the existing battery during use. This can greatly extend the time interval between complete recharges reducing the user's need to replace the battery or to plug the device in to recharge the battery. Indeed, if enough energy is harvested, it would not be necessary to recharge at all.

SUMMARY OF THE INVENTION

In one aspect the disclosure includes an apparatus for harvesting energy from motion of a prosthetic limb, wherein the prosthetic limb has motion in at least one degree of freedom. The apparatus may include a hydraulic amplifier mechanically coupled with a generator. The hydraulic amplifier includes an input member configured to receive an input motion when a first motion in a degree of freedom of the prosthetic limb causes pressure and motion of hydraulic fluid. The hydraulic amplifier may be configured to amplify the input motion of the input member to a greater output motion. The generator is configured to convert mechanical energy of the output motion into corresponding electrical energy delivered to one of an electrical load and an electrical storage reservoir.

In another aspect, the disclosure includes a prosthetic limb comprising a hydraulic cylinder and an energy harvester operably coupled with the hydraulic cylinder. The hydraulic cylinder includes hydraulic fluid and a piston slidably movable in the hydraulic cylinder in response to motion in a degree of freedom of the prosthetic limb. The energy harvester includes a hydraulic amplifier operably coupled with the piston and the generator. The hydraulic amplifier is configured to amplify an input motion of the piston to a greater output motion and to direct the output motion to the generator. The prosthetic limb further includes a generator for converting mechanical energy of the output motion into corresponding electrical energy and at least one of an electrical load and an energy storage reservoir. The electrical energy from the generator may be directed to the electrical load and/or the energy storage reservoir.

In another aspect, the disclosure includes a method of harvesting energy in a prosthetic limb. The method includes moving a prosthetic limb in a degree of freedom, slidably moving a piston in a hydraulic cylinder, in response to said movement of the prosthetic limb in the degree of freedom, to pressurize and move hydraulic fluid in said cylinder, hydraulically amplifying motion of the piston to a greater output motion, directing the output motion to a generator whereby mechanical energy of the output motion is converted into corresponding electrical energy and delivered to at least one of an electrical load and an energy storage reservoir.

DETAILED DESCRIPTION

Reference will now be made in detail to specific embodiments or features, examples of which are illustrated in the accompanying drawings. Generally, corresponding or similar reference numbers will be used, when possible, throughout the drawings to refer to the same or corresponding parts.

Figure 1:
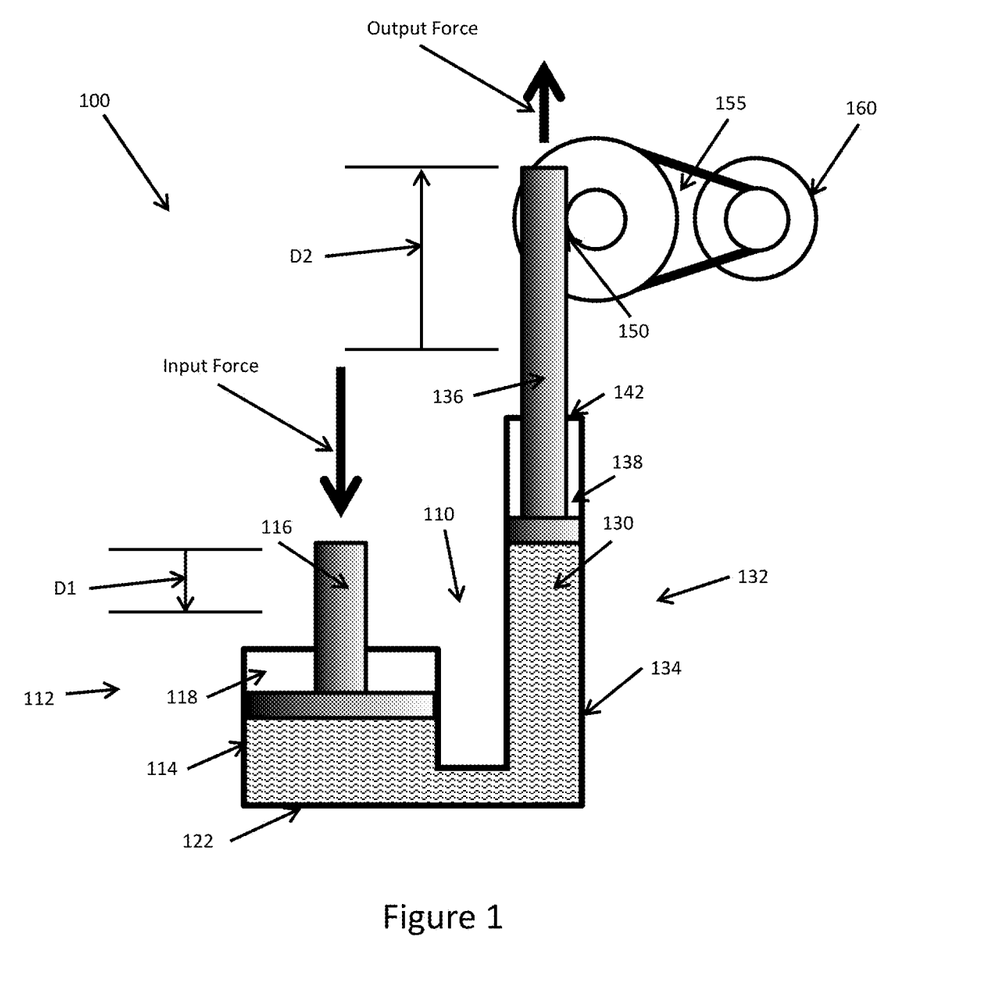
FIG. 1 illustrates an exemplary embodiment of an apparatus for harvesting energy from motion of a prosthetic limb in accordance with various aspects of the disclosure.

Referring now to FIG. 1, an exemplary embodiment of an apparatus 100 for harvesting energy from motion of a prosthetic limb is illustrated. As would be appreciated by persons skilled in the art, the prosthetic limb has motion in at least one degree of freedom. In the embodiment illustrated, the apparatus 100 includes a hydraulic amplifier 110 and a mechanical arrangement 150 configured to couple output motion and associated output force of the hydraulic amplifier 110 to a generator 160.

According to various aspects, the hydraulic amplifier 110 includes an input member 112 and an output member 132. The input member 112 may include a first hydraulic cylinder 114 and a first piston 116 slideable in the first hydraulic cylinder 114. The first piston 116 is slidably movable in the first hydraulic cylinder 114 between a first position and a second position. The first piston 116 is configured to receive an input force and an associated input motion generated when a wearer of the prosthetic transfers weight to the limb.

The output member 132 may include a second hydraulic cylinder 134 and a second piston 136 slideable in the second hydraulic cylinder 134. The second piston 136 is slidably movable in the second hydraulic cylinder 134 between a first position and a second position. The second piston 136 is configured to direct the output motion to the generator 160.

As shown in FIG. 1, the hydraulic amplifier 110 may be a closed hydraulic system. That is, the first and second hydraulic cylinders 114, 134 may be fluidly coupled via hydraulic working fluid 130 in the amplifier 110 that is essentially incompressible and cannot change volume.

According to various aspects, the first piston 116 has a face area larger than the face area of the second piston 136. For example, the area of the first piston 116 may be 2-10 times greater than the diameter of the second piston 136. However, it should be appreciated that any desired ratio between the areas of the first and second pistons may be implemented according to the disclosure. As a result, when the first piston 116 receives an input force that slidably moves the first piston a first distance D1, the second piston is displaced a proportionately greater second distance D2. Thus, the hydraulic amplifier 110 amplifies the input motion of the first piston 116 to a greater output motion of the second piston 136.

As persons skilled in the art would understand, because the two pistons and cylinders 114, 116, 134, 136 are designed with different diameters, any given input force and motion to the piston 116, 136 of one of the cylinders 114, 134, results in a force and motion output at the other cylinder which is governed by the ratio of the two piston surface areas. In other words, by making the first piston 116 and first cylinder 114 larger than the second piston 136 and second cylinder 134, the second piston 136 is forced to move farther, while the output force available at the second piston 136 is reduced. For example, if the ratio of areas is 2:1, the second piston 136 will move twice as far the first piston 116, but due to conservation of energy, the output force available at the second piston 136 will be only half as much, minus some amount lost due to the inefficiencies in the system (e.g., hydraulic fluid heating up, friction at the seals, cylinders/hoses/fittings expanding under pressure, etc.).

The generator 160 is coupled with the output member 132 of the hydraulic amplifier 110 via a mechanical arrangement 150. According to various aspects, if the generator is a linear motor, the mechanical arrangement 150 may include a direct connection between the second piston 136 and the linear motor. If the generator 160 is a rotary motor, the mechanical arrangement may include a rack-and-pinion arrangement or friction wheel connection between the second piston 136 and the rotary motor. In any case, the generator 160 is configured to convert mechanical energy of the output motion of the second piston 136 into corresponding electrical energy, which may be directed to an electrical load 162 and/or an electrical storage reservoir 164 electrically coupled with the generator 160. For example, the electrical storage reservoir may include a rechargeable battery. The generator 160 may be electrically coupled to the rechargeable battery to recharge the battery with energy harvested from input motion applied to the input member 112 of the apparatus 110 by a wearer of the prosthetic during use.

According to various aspects, the electrical load 162 may include a microprocessor control circuit, an electric motor for operating a valve or other actuator, or an electric motor for adjusting the motion of or providing propulsive power to the limb. According to various aspects, the electrical storage reservoir may include a rechargeable battery, a capacitor, or other energy storage device, coupled with a circuit designed to condition the power coming from the generator 160 to be provided as an input to the storage reservoir 164.

It should be appreciated that in some aspects the output motion of the second piston 136 may be further amplified by an additional set of motion amplification stages, which would gear up the speed input to the generator 160. Such amplification can be accomplished, for example, by taking output motion of a rack-and-pinion arrangement 150 coupled with the second piston 136 and amplifying this output motion through a quiet timing belt-and-pulley arrangement 155 or other equivalent mechanism, as would be understood by persons skilled in the art. According to various aspects, the generator 160 may include an electromagnetic motor having a generator mode.

Referring again to FIG. 1, the harvesting apparatus 100 may include a return spring configured to return the first and second pistons 116, 136 to their respective neutral positions during the swing phase of a user's stride so that the apparatus 100 is ready to operate again on the user's next step. According to various aspects of the disclosure, the first hydraulic cylinder 112 may include a first chamber 118 on the rod-side of the first piston 116. The second hydraulic cylinder 132 may include a second chamber 138 on the rod-side of the second piston 136. The first and second chambers 118, 138 include pre-charge volumes of air, which are used as air springs to force the pistons back to their first positions. For example, as the second piston 136 approaches the top 142 of the second cylinder 132, as viewed in FIG. 1, the air volume in the second chamber 138 above the second piston 136 is compressed creating a spring return force. This spring return force works to push the first and second pistons 116, 136 of the hydraulic amplifier 110 back to their neutral positions. In certain prosthetic devices, forces exerted by the user's motion cause a complete motion cycle. The return spring described here is required for prosthetic devices that only achieve an incomplete motion cycle from the user input. In either case, energy may be harvested during this return motion as well as the initial motion.

The volume of air in the first chamber 118 behind the first piston 116 also contributes to this spring effect by complementing the spring force above the second piston 136. As the user/wearer of the prosthetic provides an input force to the input member 112, the first piston 116 moves toward the bottom 122 of the first cylinder 112 and the volume of the first chamber 118 above the first piston 116 increases, thereby creating a lower pressure (in some situations below atmospheric pressure) n the first chamber 118 which works to pull the first cylinder back to its neutral position. It should be appreciated that both of these contributors to the spring effect can be included or only one or the other can be utilized, depending on the requirements of the application. If only one air spring is needed, one possible embodiment would be to leave the chamber of one of the cylinders open to atmosphere so that the pressure of air space above that piston remained essentially constant (at atmospheric pressure) and does not contribute to the spring effect.

Figure 2:
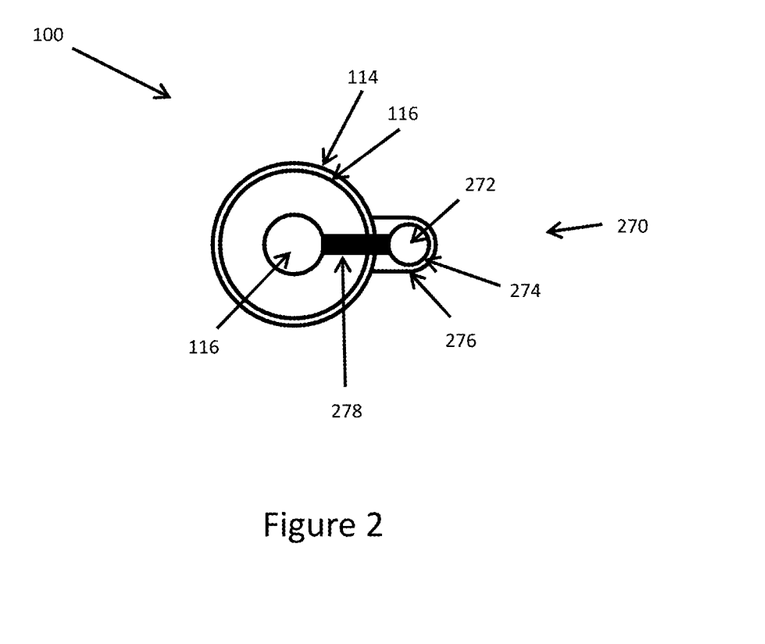
FIG. 2 illustrates an exemplary embodiment of an anti-rotation device for use with an apparatus for harvesting energy from motion of a prosthetic limb in accordance with various aspects of the disclosure.

Referring now to FIG. 2, according to another aspect, the harvesting apparatus 100 may include an anti-rotation mechanism 270, which limits the rotational motion of the first piston 116 in the first hydraulic cylinder 114 to prevent the wearer's prosthetic limb from rotating out of proper alignment. For example, the anti-rotation mechanism 270 may include a torsion member 272, for example, a shaft or a rod, substantially parallel to the axis of and rigidly attached to the first piston 116. The torsion member 272 slides through an opening 274 in a torsion resistor 276, which is rigidly attached and stationary relative to the first cylinder 114. The mechanism 270 allows the first piston 116 to move linearly but prevents it from rotating within the first cylinder 114. A similar effect could be achieved by having a piston and cylinder, or a feature on the piston and cylinder, which are not circular, and thus resist rotational motion.

Varying the stiffness of the torsion resistor 276 has a constant effect on the torsional stiffness of the system regardless of the stroke position of the piston. However, varying the stiffness of the torsion shaft does have an effect on torsional stiffness which varies throughout the stroke of the piston. That is, the torsion shaft would have a stronger resistance to torsional deflection when it is compressed (positioned near the bottom of the cylinder) than when it is extended (positioned near the top of the cylinder).

Referring now to FIGS. 3A thru 4B, exemplary embodiments of an apparatus 300 for harvesting energy from motion of a prosthetic knee and an apparatus 400 for harvesting energy from motion of a prosthetic ankle are illustrated. As would be appreciated by persons skilled in the art, the prosthetic knee has motion in at least one degree of freedom. In the embodiment illustrated, the apparatus 300 includes a hydraulic amplifier 310 and a mechanical arrangement 350 configured to couple output motion and associated output force of the hydraulic amplifier 310 to a generator 360.

According to various aspects, the hydraulic amplifier 310 includes an input member 312 and an output member 332. The input member 312 may include a first hydraulic cylinder 314 and a first piston 316 slideable in the first hydraulic cylinder 314. The first piston 316 is slidably movable in the first hydraulic cylinder 314 between a first position and a second position. The first piston 316 is configured to receive an input force and an associated input motion generated when a wearer of the prosthetic transfers weight to the limb.

The output member 332 may include a second hydraulic cylinder 334 and a second piston 336 slideable in the second hydraulic cylinder 334. The second piston 336 is slidably movable in the second hydraulic cylinder 334 between a first position and a second position. The second piston 336 is configured to direct the output motion to the generator 360.

As shown in FIG. 1, the hydraulic amplifier 310 may be a closed hydraulic system. That is, the first and second hydraulic cylinders 314, 334 may be fluidly coupled via hydraulic working fluid 330 in the amplifier 310 that is essentially incompressible and cannot change volume.

According to various aspects, the first piston 316 has a face area larger than the face area of the second piston 336. For example, the area of the first piston 316 may be 2-10 times greater than the diameter of the second piston 336. However, it should be appreciated that any desired ratio between the areas of the first and second pistons may be implemented according to the disclosure. As a result, when the first piston 316 receives an input force that slidably moves the first piston a first distance, the second piston is displaced a proportionately greater second distance. Thus, the hydraulic amplifier 310 amplifies the input motion of the first piston 316 to a greater output motion of the second piston 336.

As persons skilled in the art would understand, because the two pistons and cylinders 314, 316, 334, 336 are designed with different diameters, any given input force and motion to the piston 316, 336 of one of the cylinders 314, 334, results in a force and motion output at the other cylinder which is governed by the ratio of the two piston surface areas. In other words, by making the first piston 316 and first cylinder 314 larger than the second piston 336 and second cylinder 334, the second piston 336 is forced to move farther, while the output force available at the second piston 336 is reduced. For example, if the ratio of areas is 2:1, the second piston 336 will move twice as far the first piston 316, but due to conservation of energy, the output force available at the second piston 336 will be only half as much, minus some amount lost due to the inefficiencies in the system (e.g., hydraulic fluid heating up, friction at the seals, cylinders/hoses/fittings expanding under pressure, etc.).

The generator 360 is coupled with the output member 332 of the hydraulic amplifier 310 via a mechanical arrangement 350. According to various aspects, if the generator is a linear motor, the mechanical arrangement 350 may include a direct connection between the second piston 336 and the linear motor. If the generator 360 is a rotary motor, the mechanical arrangement may include a rack-and-pinion arrangement or friction wheel connection between the second piston 336 and the rotary motor. In any case, the generator 360 is configured to convert mechanical energy of the output motion of the second piston 336 into corresponding electrical energy, which may be directed to an electrical load 362 and/or an electrical storage reservoir 364 electrically coupled with the generator 360. For example, the electrical storage reservoir may include a rechargeable battery. The generator 360 may be electrically coupled to the rechargeable battery to recharge the battery with energy harvested from input motion applied to the input member 312 of the apparatus 310 by a wearer of the prosthetic during use.

According to various aspects, the electrical load 362 may include a microprocessor control circuit, an electric motor for operating a valve or other actuator, or an electric motor for adjusting the motion of or providing propulsive power to the limb. According to various aspects, the electrical storage reservoir 364 may include a rechargeable battery, a capacitor, or other energy storage device, coupled with a circuit designed to condition the power coming from the generator 360 to be provided as an input to the storage reservoir 364.

It should be appreciated that in some aspects the output motion of the second piston 336 may be further amplified by an additional set of motion amplification stages, which would gear up the speed input to the generator 360. Such amplification can be accomplished, for example, by taking output motion of a rack-and-pinion arrangement 350 coupled with the second piston 336 and amplifying this output motion through a quiet timing belt-and-pulley arrangement 355 or other equivalent mechanism, as would be understood by persons skilled in the art. According to various aspects, the generator 360 may include an electromagnetic motor having a generator mode.

Since the use of a prosthetic knee or ankle requires the wearer to provide bi-directional forces in a degree of freedom, hydraulic working fluid may be provided on both sides of the first and second pistons 116, 136 in a closed hydraulic system. Therefore, force and motion in a first direction of the degree of freedom will cause movement of the first and second pistons 116, 136 from a first position toward a second position, while force and motion in a second direction, opposite to the first direction, will cause the first and second pistons 116, 136 to return toward the first position. Therefore, energy can be harvested from the amplifier in either one or both directions of travel of the pistons 116, 136.

Referring again to FIGS. 3A thru 4B, the harvesting apparatus 300 may include a number of attachment points 380 for coupling the apparatus 300 to a prosthetic knee, as a well as a number of pivot points 382 allowing pivotal motion of the harvesting apparatus 300 relative to the prosthetic. Similarly, the harvesting apparatus 400 may include a number of attachment points 480 for coupling the apparatus 400 to a prosthetic ankle, as a well as a number of pivot points 482 allowing pivotal motion of the harvesting apparatus 400 relative to the prosthetic.

Figure 3A:
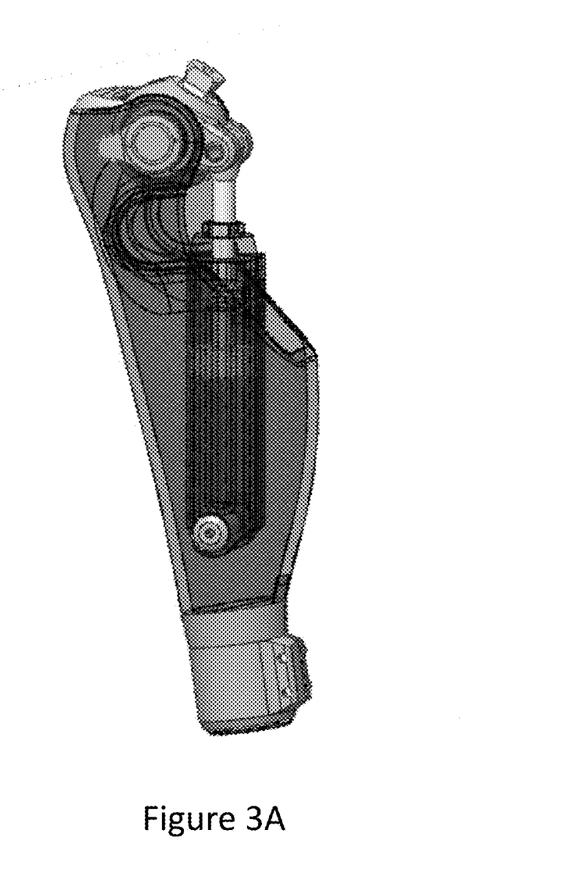
FIG. 3A illustrates an exemplary prosthetic knee.
Figure 3B:
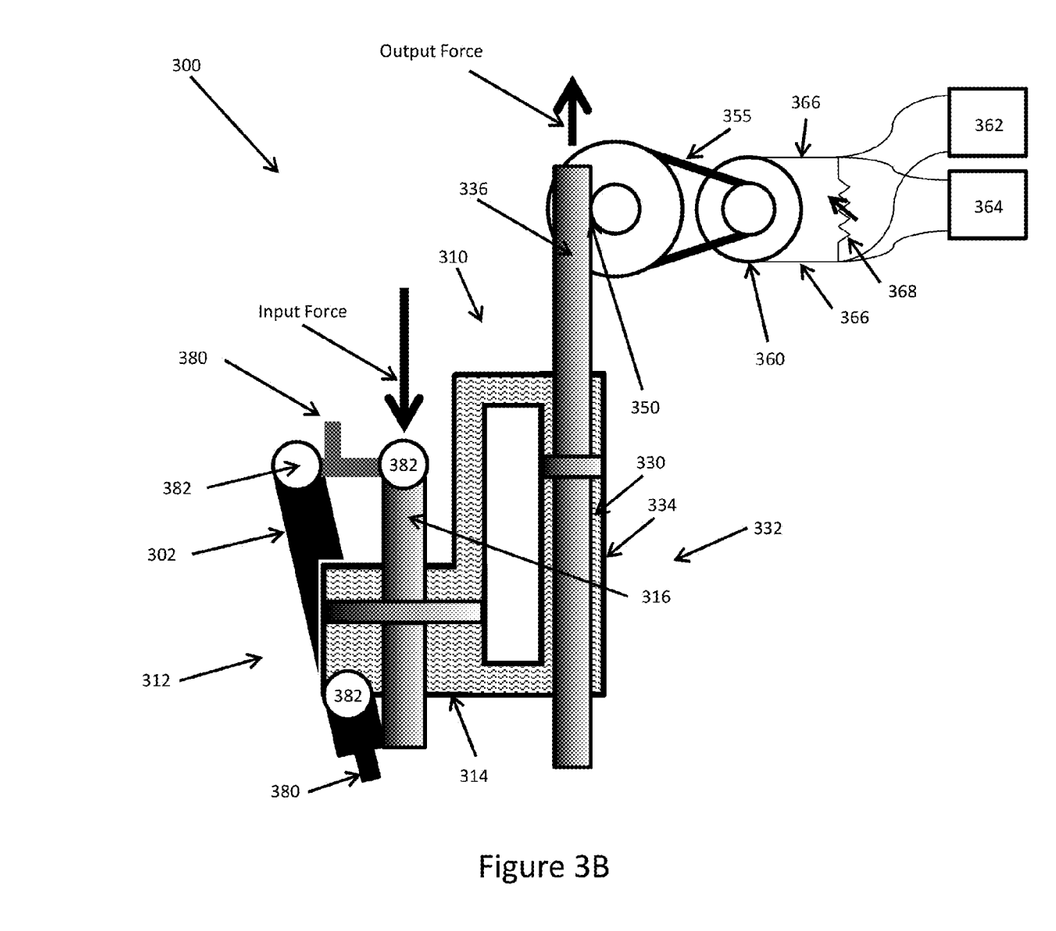
FIG. 3B illustrates an exemplary embodiment of an apparatus for harvesting energy from motion of a prosthetic knee in accordance with various aspects of the disclosure.
Figure 4A:
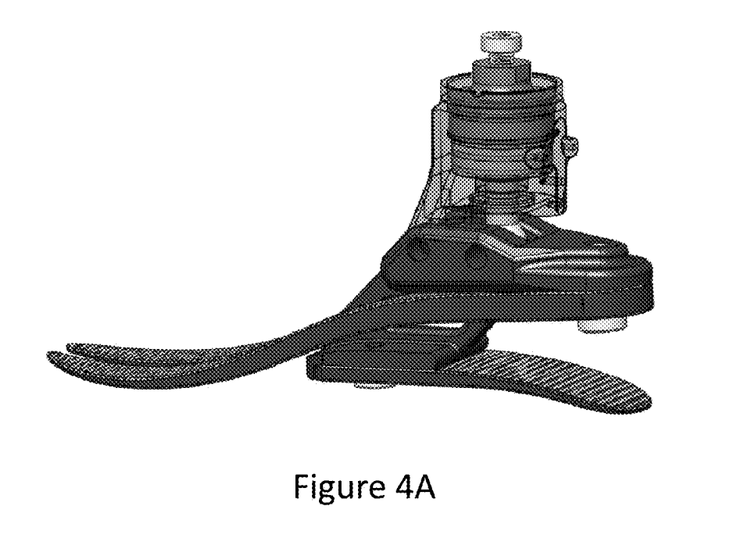
FIG. 4A illustrates an exemplary prosthetic ankle.
Figure 4B:
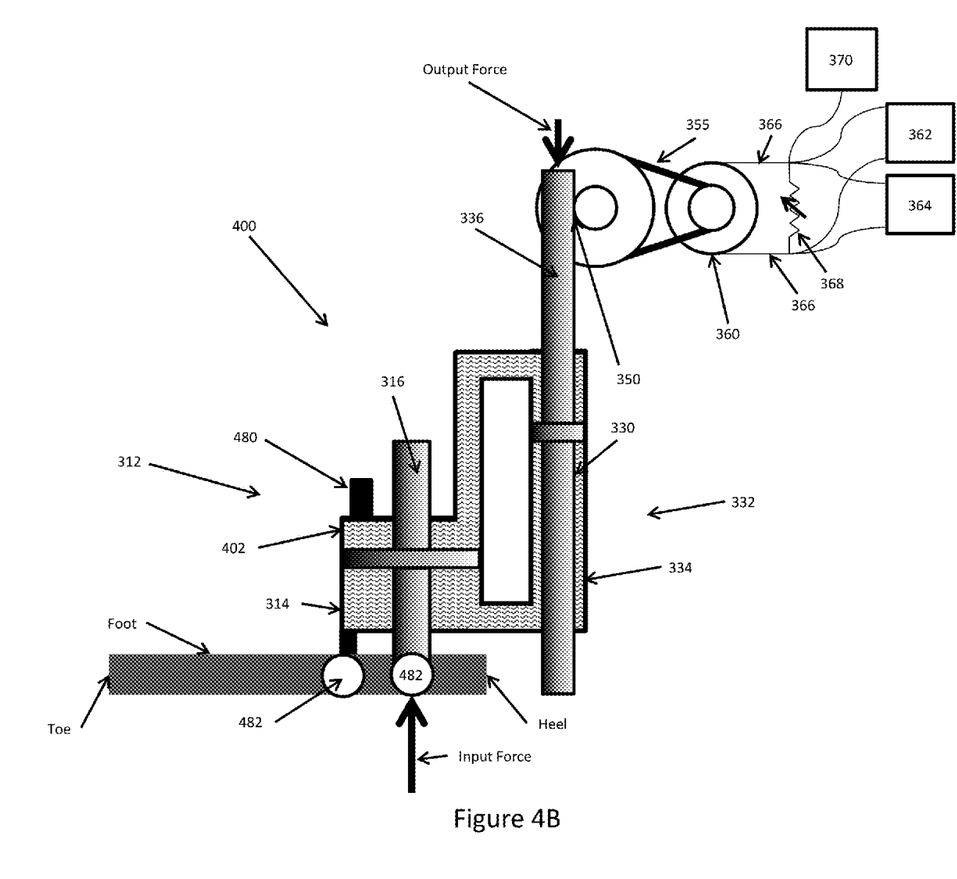
FIG. 4B illustrates an exemplary embodiment of an apparatus for harvesting energy from motion of a prosthetic ankle in accordance with various aspects of the disclosure.

Referring now to FIGS. 3B and 4B, the generator 360 may include terminals 366 across which a variable-impedance energy harvesting circuit 368 may extend. When higher impedance (resistance) is applied across the terminals 366, the motor is able to turn more easily, and when a lower resistance is applied across the terminals 366, the motor is more difficult to turn. Thus, with the higher resistance across the terminals 366, the prosthetic limb will be more free to deflect and will feel softer to the wearer. On the other hand, with the lower resistance across the terminals 366, the limb will be more resistant to deflection and will feel stiffer to the wearer. It should be appreciated that the embodiment of FIG. 1 may include a variable-impedance energy harvesting circuit across its terminals similar to that shown in FIGS. 3B and 4B in order to vary the deflection and feel of the prosthetic limb.

It should be appreciated that one or more of the aforementioned embodiments may include additional components including, but not limited to, sensors, microprocessor controllers, valves, and actuators configured to assist the wearer's gait motion. One or more of the embodiments may include a joint member (e.g., piston 116, piston 316) and an arrangement for controlling motion of the joint member. One or more of the embodiments may include an arrangement configured to actively propel the wearer forward. Further, one or more of the aforementioned components and arrangements may be powered by the energy storage reservoir. present disclosure is related to copending U.S. patent application.

In operation, energy may be harvested from a prosthetic limb by moving a prosthetic limb in a degree of freedom, slidably moving a piston in a hydraulic cylinder, in response to the movement of the prosthetic limb in the degree of freedom, to pressurize and move hydraulic fluid in said cylinder, and hydraulically amplifying motion of the piston to a greater output motion. The output motion may be directed to a generator configured to convert mechanical energy of the output motion into corresponding electrical energy and direct the electrical energy to an electrical load and/or an energy storage reservoir.

Industrial Applicability

As mentioned above, only a small amount of deflection is tolerable in a prosthetic limb. This small deflection is not enough to generate an appreciable amount of electrical energy when made available to an electromechanical generator. Simply amplifying the deflection would generate a force that is often too large for the small electromechanical components used in prosthetics and would not rotate an electromechanical generator enough to generate a useful amount of energy. Therefore, a hydraulic amplifier is designed to transform the small amount of tolerable deflection into a large amount of motion for running an electromechanical generator while reducing the amount of force at the output of the amplifier to a force that is more appropriate for the small components capable of being used in prosthetics. This design is then configured to properly match the mechanical impedance of the generator being used to source energy to the storage system.

From the foregoing, it will be appreciated that, although specific embodiments have been described herein for purposes of illustration, various modifications or variations may be made without deviating from the spirit or scope of inventive features claimed herein. Other embodiments will be apparent to those skilled in the art from consideration of the specification and figures and practice of the arrangements disclosed herein. It is intended that the specification and disclosed examples be considered as exemplary only, with a true inventive scope and spirit being indicated by the following claims and their equivalents.

What is claimed is:

1. An apparatus for harvesting energy from motion of a prosthetic limb, the prosthetic limb having motion in at least one degree of freedom, the apparatus comprising:
a hydraulic amplifier including an input member configured to receive an input displacement when a first motion in a degree of freedom of the prosthetic limb causes pressure and motion of hydraulic fluid, the hydraulic amplifier being configured to amplify the input displacement of the input member to a greater output displacement; and
a generator mechanically coupled with the hydraulic amplifier, the generator being configured to convert mechanical energy of the output displacement into corresponding electrical energy delivered to one of an electrical load and an electrical storage reservoir.

2. The apparatus of claim 1, wherein the hydraulic amplifier comprises:
a first piston slidably movable in a first hydraulic cylinder between a first position and a second position, the first piston being associated with the input member so as to receive the input displacement;
a second piston slidably movable in a second hydraulic cylinder between a first position and a second position, the second piston is configured to direct the output displacement to the generator.

3. The apparatus of claim 2, wherein the first piston is configured to move a first distance in response to the input displacement, the movement of the first piston by the first distance causing the second piston to move a second distance, the second distance being greater than the first distance.

4. The apparatus of claim 3, wherein the hydraulic amplifier comprises a closed hydraulic system using an effectively incompressible working hydraulic fluid, and the first hydraulic cylinder has a diameter larger than a diameter of the second hydraulic cylinder.

5. The apparatus of claim 2, further comprising a return spring configured to return the first and second pistons to their respective first positions.

6. The apparatus of claim 2, wherein a second motion in the degree of freedom of the prosthetic limb opposite to said first motion causes pressure and motion of the hydraulic fluid configured to return the first and second pistons to their respective first positions.

7. The apparatus of claim 2, further comprising a torsion resistant arrangement configured to couple the first piston to the first hydraulic cylinder such that the first piston is prevented from rotating within the first hydraulic cylinder.

8. The apparatus of claim 7, wherein the torsion resistant arrangement prevents undesired rotational motion within the prosthetic limb.

9. The apparatus of claim 1, wherein the generator comprises an electromagnetic motor having a generator mode.

10. The apparatus of claim 9, further comprising a variable-impedance energy harvesting circuit across terminals of the motor.

11. The apparatus of claim 10, wherein higher electrical impedance across the terminals allows the motor to turn more easily, while a lower resistance across the terminals makes the motor more difficult to turn.

12. The apparatus of claim 11, wherein with the higher electrical impedance, the prosthetic limb will be more free to deflect and will feel softer to the wearer, while with the lower resistance, the limb will be more resistant to deflection and will feel stiffer to the wearer.

13. The apparatus of claim 1, wherein the generator comprises one of a rotary motor and a linear motor.

14. The apparatus of claim 1, wherein the output displacement is amplified before reaching the generator.

15. The apparatus of claim 1, wherein the electrical storage reservoir comprises a rechargeable battery, the generator being electrically coupled to the battery to recharge the battery with energy harvested from the input displacement of a wearer during use.

16. A prosthetic limb, comprising:
a hydraulic cylinder including hydraulic fluid and a piston slidably movable in the hydraulic cylinder in response to motion in a degree of freedom of the prosthetic limb;
an energy harvester operably coupled with the hydraulic cylinder, the energy harvester including a hydraulic amplifier operably coupled with the piston and a generator, the hydraulic amplifier being configured to amplify an input displacement of the piston to a greater output displacement and to direct the output displacement to the generator, the generator being configured to convert mechanical energy of the output displacement into corresponding electrical energy; and
at least one of an electrical load and an energy storage reservoir, the electrical energy from the generator being directed to said at least one of the electrical load and the energy storage reservoir.

17. The prosthetic limb of claim 16, further comprising at least one component selected from sensors, microprocessor controllers, valves, and actuators configured to assist a wearer's gait motion, said at least one component being powered by the energy storage reservoir.

18. The prosthetic limb of claim 16, further comprising a joint member, which includes the piston, and an arrangement for controlling motion of the joint member, the arrangement including at least one component powered by the energy storage reservoir.

19. The prosthetic limb of claim 16, further including an arrangement configured to actively propel a wearer forward, the arrangement including at least one component powered by the energy storage reservoir.

20. A method of harvesting energy in a prosthetic limb, the method comprising:
moving a prosthetic limb in a degree of freedom;
slidably moving a piston in a hydraulic cylinder, in response to said movement of the prosthetic limb in the degree of freedom, to pressurize and move hydraulic fluid in said cylinder;
hydraulically amplifying displacement of the piston to a greater output displacement; and
directing the output displacement to a generator whereby mechanical energy of said output displacement is converted into corresponding electrical energy and directed to at least one of an electrical load and an energy storage reservoir.

* * * * *